United States Patent
Kawabata et al.

(10) Patent No.: US 7,074,427 B2
(45) Date of Patent: Jul. 11, 2006

(54) MEDICINE, CARRIER FOR MEDICINE, METHOD OF PRODUCING MEDICINE, AND METHOD OF TUMOR TREATMENT

(75) Inventors: Kenichi Kawabata, Kodaira (JP); Shinichiro Umemura, Hachioji (JP); Kazuaki Sasaki, Kawasaki (JP)

(73) Assignee: Hitachi, Ltd., Tokyo (JP)

( * ) Notice: Subject to any disclaimer, the term of this patent is extended or adjusted under 35 U.S.C. 154(b) by 76 days.

(21) Appl. No.: 10/198,178

(22) Filed: Jul. 19, 2002

(65) Prior Publication Data

US 2003/0143161 A1 Jul. 31, 2003

(30) Foreign Application Priority Data

Jan. 30, 2002 (JP) ............................. 2002-022254

(51) Int. Cl.
*A61K 9/48* (2006.01)
*A61K 9/14* (2006.01)
*A61K 9/16* (2006.01)
*A61K 9/50* (2006.01)

(52) U.S. Cl. ............... 424/451; 424/489; 424/490; 424/491; 424/497; 424/499

(58) Field of Classification Search ............. 424/451, 424/489, 490, 491, 497, 499
See application file for complete search history.

(56) References Cited

U.S. PATENT DOCUMENTS

| | | | |
|---|---|---|---|
| 5,498,421 A | * | 3/1996 | Grinstaff et al. ............ 424/450 |
| 5,523,058 A | | 6/1996 | Umemura et al. |
| 6,041,253 A | * | 3/2000 | Kost et al. ................... 604/20 |
| 6,156,337 A | * | 12/2000 | Barenholz et al. .......... 424/450 |
| 6,258,378 B1 | * | 7/2001 | Schneider et al. .......... 424/450 |

FOREIGN PATENT DOCUMENTS

| | | |
|---|---|---|
| JP | 01-146829 | 6/1989 |
| JP | 2-126848 | 5/1990 |
| JP | 04-054132 | 2/1992 |
| JP | 05-078260 | 3/1993 |
| JP | 6-29196 | 4/1994 |
| JP | 11-322633 | 11/1999 |
| WO | WO98/1131 | 1/1998 |

OTHER PUBLICATIONS

Ultrasound in Medicine & Biology, vol. 23, 1997, pp. 1405-1412, Dalecti et al.
Japan Journal of Cancer Research, vol. 84, May, 1993, S. Umemura et al., pp. 582-586.
Ultrasonics, vol. 26, 1988, A. Atchley, pp. 280-285.
American Journal of Cardiology, vol. 81, E.C. Unger et al., p. 58. (1998).

* cited by examiner

*Primary Examiner*—Humera N. Sheikh
(74) *Attorney, Agent, or Firm*—Mattingly, Stanger, Malur & Brundidge, P.C.

(57) ABSTRACT

A medicinal preparation capable of lowering the threshold of cavitation and generating active oxygen species via acoustic cavitation caused by an ultrasound is provided. The preparation, which is to be used in combination with ultrasonic irradiation, comprises a shell within the internal space of which a gas is enclosed and which contains or retains a substance capable of generating active oxygen species upon ultrasonic irradiation of the shell.

3 Claims, 10 Drawing Sheets

FIG. 7

| MEDICINE | | RATE OF TUMOR GROWTH INHIBITION(%) | |
|---|---|---|---|
| CARRIER | AGENT | WITHOUT ULTRASOUND | WITH ULTRASOUND |
| ALBUMIN | HEMATOPORPHYRIN DIMER | 2.5 | 70.5 |
| CONTROL | | 0 | 10.2 |

FIG. 9

| MEDICINE | | RATE OF TUMOR GROWTH INHIBITION(%) | |
|---|---|---|---|
| CARRIER | AGENT | WITHOUT ULTRASOUND | WITH ULTRASOUND |
| HEMOGLOBIN | ROSE BENGAL | 0.5 | 60.2 |
| CONTROL | | 0 | 10.2 |

MEDICINE, CARRIER FOR MEDICINE, METHOD OF PRODUCING MEDICINE, AND METHOD OF TUMOR TREATMENT

This application claims foreign priority to Japanese Application No. 2002-022254 filed Jan. 30, 2002.

BACKGROUND OF THE INVENTION

1. Field of the Invention

The present invention relates to a medicine, a carrier for the medicine, and a method of treatment using the medicine, with or by which acoustic cavitation is caused by ultrasonic radiation and treatment or diagnosis is carried out by the action thereof.

2. Description of the Related Art

The treatment of malignant tumors by extracorporeal radiation of a focused ultrasound is less invasive and in principle superior with respect to physical strength declining and postoperative quality of life of patients as compared with surgical operation and the social value thereof is expected to be going up in the future. The treatment using a focused ultrasound includes two classes, namely thermal treatment which comprises raising the temperature of the affected part through absorption of the ultrasound by the relevant tissue, and chemical one utilizing the interaction between a chemical substance and the ultrasound. A method of treatment which belongs to the latter class and uses a substance capable of generating active oxygen species upon ultrasonic irradiation has been proposed by Umemura et al. (S. Umemura, et al.: Jpn J. Cancer Res., vol. 84, pp. 582–586 (1993)) and is called sonodynamic cancer treatment.

In sonodynamic cancer treatment acoustic cavitation is thought to play an important role in producing therapeutic effects. For this purpose, methods using physical means have so far exclusively been proposed for efficiently causing nucleation and collapse of acoustic cavitation. Thus, JP-A-H02-126848 (1990) describes a technology which comprises irradiating ultrasonic waves while changing the sound field at intervals of 1 to 100 msec. Taking notice of the fact that the ultrasonic irradiation time required for the nucleation of acoustic cavitation is 1 to 100 msec, this technology instructs that ultrasonic irradiation be made while changing the sound field from one to the other differing in wave front at such time intervals so that the acoustic cavitation nucleated by one sound field may be collapsed by the other sound field and this cycle may be repeated. By doing so, it becomes possible to improve the efficiency of acoustochemical effects by an order of magnitude as compared with the case where the sound field is not changed at the same ultrasonic power level. Further, in U.S. Pat. No. 5,523,058, there is described a technology according to which a wave form favorable to acoustic cavitation nucleation, which can generally be obtained in the presence of a reflector, can be obtained even when there is no reflector. According to this technology, a waveform favorable to acoustic cavitation nucleation is obtained by superposing one frequency component and the second harmonic component thereof on each other. Since when ultrasonic irradiation is applied to a patient, the reflector effect cannot always be expected, it is expected that this technology will contribute to the enhancement of effects and the improvement in safety in the ultrasonic irradiation treatment.

Further, in JP-B-H06-29196 (1994), there is described a method of chemically enhancing the antitumor effect of ultrasound which comprises using a substance capable of forming active oxygen species when exposed to the chemical action of ultrasound. The substances, for example porphyrin, used in this technology secondarily generate active oxygen species due to acoustic cavitation caused by ultrasonic waves. However, they cannot lower the cavitation threshold. On the contrary, WO 98/01131 describes a technique of lowering the cavitation threshold by means of an amphiphilic xanthene dye and causing acoustic cavitation by ultrasonic waves to thereby cause secondary generation of active oxygen species by the dye.

In the field of ultrasonic diagnosis, microbubble contrast agents comprising air or gas bubbles with low solubility as covered by a shell made of a protein, a surface active agent and/or the like are widely used. These contrast agents are effective in lowering the threshold of acoustic cavitation, as reported by A. A. Atchley in Ultrasonics, vol. 26, pp. 280–285 (1988). Using this property, E. C. Unger et al. proposed, in Am. J. Cardiol., vol. 81, p. 58, a thrombosis treatment agent comprising such a contrast agent and a thrombus-selective peptide bound to the surface of the contrast agent and intended to be used in combination with ultrasound. However, although such microbubbles themselves can facilitate the cavitation, they are not physiologically active in generating active oxygen species or the like upon ultrasonic irradiation. In their application in such thrombosis treatment agents as mentioned above, it is necessary to use them in combination with a thrombolytic agent. Furthermore, those bubbles which have a diameter of several micrometers and are effective as a contrast agent do not migrate from blood vessels to other organs, so that when the microbubble contrast agents known in the art are used as such, it is difficult to apply them to sites other than intravascular sites.

As mentioned above, some technologies have been proposed for efficiently producing biological actions of acoustic cavitation. By the way, a therapeutic agent to be used in sonodynamic treatment is required to have three functions, namely (1) the ability to accumulate to the tumor site, (2) the ability to lower the threshold of acoustic cavitation and (3) the ability to generate active oxygen species upon exposure to acoustic cavitation caused by ultrasonic waves. This requirement is partially satisfied by the method disclosed in WO 98/01131, namely the method comprising lowering the cavitation threshold by means of an amphiphilic xanthene dye and causing acoustic cavitation by ultrasonic waves to thereby cause secondary generation of active oxygen species by the dye. However, this method intends to make one substance perform the above three functions. Therefore, in particular in the function in secondarily generating active oxygen species in response to ultrasound-caused cavitation, the above dye is inferior to porphyrin dyes. This poses a problem.

On the other hand, stabilized bubbles produced by stabilizing air or gas bubbles with low solubility in water by means of a shell consisting of a protein or a surface active agent, when used as a contrast medium, show an effect of lowering the sound intensity for causing cavitation within blood vessels and therefore are expected to be applicable to intravascular treatment in combination with an appropriate drug. However, the drug so far combined with such stabilized gas is a thrombolytic agent or a DNA, and such drug does not particularly interact with cavitation but cavitation is only indirectly involved in the treatment, for example by promoting drug penetration into the affected part.

SUMMARY OF THE INVENTION

In view of such problems in the prior art as mentioned above, it is an object of the present invention to provide a medicinal or pharmaceutical preparation suited for use in sonodynamic treatment which has the three functions, namely (1) the ability to accumulate to the tumor site, (2) the ability to lower the threshold of acoustic cavitation and (3) the ability to generate active oxygen species in response to acoustic cavitation caused by ultrasonic waves. Another object of the invention is to provide a tumor treatment method which uses the above medicinal preparation.

The present inventors made intensive investigations from the viewpoint that a medicinal preparation, comprising a stabilized gas effective in lowering the sound intensity for causing cavitation and a component capable of generating active oxygen species in response to cavitation would be favorable. As a result, they noticed that the above objects can be accomplished by a medicinal preparation which comprises a stabilized gas, which is air or a sparingly soluble gas, stabilized by a shell made of a protein, a surface active agent or the like, and a medicinally active substance which is disposed in the shell phase and is lipophilic and capable of generating active oxygen species via acoustic cavitation caused by ultrasonic waves.

When minute particles such as bubbles are systemically administered into a human body, the site of occurrence thereof in the body generally varies according to the size of the minute particles. As described in Mitsuru Hashida and Yoshinobu Takakura: "Seitainai Yakubutu Sotatsu-gaku (In vivo drug delivery study)" (published 1996 by Sangyo Tosho), for instance, bubbles having a diameter of 1 to 10 µm, which are used as a contrast agent for ultrasonic diagnosis, mainly occur in blood vessels and liver. Minute particles submicron in size are accumulated at a tumor site.

FIG. 1 is a schematic representation of the normal process of acoustic cavitation, which includes the steps of nucleation, growth, resonance and collapse. Stabilized bubbles having a diameter of 1 to 10 µm can resonate with the frequencies of 1 to 10 MHz, which are generally used in ultrasonic diagnosis. When bubbles of this size are used, the effects of cavitation can be produced directly in the step of collapse without following the process including nucleation, growth and collapse. Thus, cavitation can be caused with a smaller quantity of ultrasonic energy. Based on such principle, stabilized bubbles are effective in lowering the threshold of cavitation, as described in Ultrasonics, vol. 26, pp. 280–285 (1988). The protein or surface active agent, which is the material forming the shell of stabilized gas is generally known to interact with a lipophilic substance to form a complex. The medicinally active substance capable of generating active oxygen species is generally lipophilic, and the complex of the shell material with the medicinally active, lipophilic substance capable of generating active oxygen species via cavitation serves to allow cavitation to occur at a lower sound intensity owing to occurrence of the stabilized bubbles and, upon occurrence of cavitation, sever to generate active oxygen species owing to the presence of the medicinally active substance capable of generating active oxygen species via acoustic cavitation. Thus, when bubbles having a diameter of 1 to 10 µm are used as stabilized bubbles and applied to blood vessels, the thrombolytic and other effects, or the effects of destructing nutrient vessels for a tumor tissue and thus preventing the feeding of the tumor tissue can be produced without relying upon a thrombolytic agent or tumor tissue blocking agent.

When the diameter of stabilized bubbles is smaller than 1 µm, cavitation occurs via the above-mentioned steps of growth, resonance and collapse, hence the effect of causing cavitation immediately from the step of collapse cannot be produced, unlike the case where the diameter is 1 µm or larger. However, by using stabilized bubbles as the nuclei shown in FIG. 1, it is possible to produce the effects of cavitation through the steps of growth, resonance and collapse, bypassing the step of nucleation, so that the ultrasound intensity necessary for cavitation lowers. Further, stabilized bubbles submicron in size are accumulated at a tumor site, so that a medicinal preparation for sonodynamic treatment capable of being accumulated at a tumor site and capable of lowing the threshold of cavitation can be obtained.

The ultrasonic irradiation method described in U.S. Pat. No. 5,523,058 and comprising superposing a fundamental wave and its second harmonic component on each other promotes the process of bubble growth, hence is suited for combination with stabilized bubbles submicron in size. According to a report by Delecki et al. (Ultrasound in Med. & Biol., vol. 23, pp. 1405–1412 (1997)), the microbubble ultrasonic contrast agent Albunex (registered trademark), which is known to be stably present in vivo only for several minutes, lowers the threshold of cavitation in vivo even at several hours after administration. The shell constituting Albunex (registered trademark) is made of a denatured albumin and the possibility of the shell remaining as a remnant after disintegration of each bubble is high as compared with the possibility of its forming a small bubble like a surface active agent. This shell remnant is a protein aggregate and, by forming protein aggregates submicron in size, it is possible to lower the threshold of cavitation and cause them to accumulate at a tumor site.

Based on the above considerations, the present inventors made investigations in search of a protein and a surface active agent administrable to the living body and, as a result, have now completed the present invention.

Thus, the medicinal preparation according to the invention, which is to be used in combination with ultrasonic irradiation, is characterized in that it comprises a shell, a gas enclosed in the internal space of the shell and a substance capable of generating active oxygen species upon ultrasonic irradiation as contained in the shell. This medicinal preparation is used in combination with ultrasonic irradiation.

The gas to be enclosed in the internal space of the shell may be air or gasessparingly soluble in water. The substance capable of generating active oxygen species upon ultrasonic irradiation may be retained on the surface of the shell or within the shell.

The shell may have a spherical shell form with an outside diameter of not smaller than 0.1 µm but not larger than 5 µm. By using stabilized bubbles not smaller than 0.1 µm but not larger than 1 µm in outside diameter as the medicinal preparation, it is possible to accumulate them at a tumor site.

The material constituting the shell is preferably a protein, in particular a surface active protein. The surface active protein is not particularly restricted but may be any of those proteins which are low in toxicity to the living body. Albumin, LDL and hemoglobin, which are abundant in blood, are particularly desirable. In some uses, proteins which do not occur in blood but are highly capable of causing foaming, such as saponin and protein Z, also can form shells with ease, hence can be used as the shell materials.

A surface active agent may also be used as a shell-constituting material. The surface active agent is not particularly restricted but one low in toxicity to humans is suited for use, hence a phospholipid is desirably used.

The substance capable of generating active oxygen species upon ultrasonic irradiation, which is to be retained on or in the shell, may be either a photosensitizable antitumor agent or a photosensitizable dye (e.g. xanthene dye, porphyrin dye). The pharmaceutical carrier, or carrier for medicinal preparations, according to the invention is a carrier for retaining a medicinal component and intended for use in combination with ultrasonic irradiation, which is characterized in that a shell not smaller than 0.1 μm but not greater than 5 μm in outside diameter and a gas enclosed therein and occurring in a gaseous state. When pharmaceutical carriers not smaller than 0.1 μm but not greater than 1 μm are used, the medicinal component can be accumulated at a tumor site.

The method of producing the medicinal preparation for use in combination with ultrasonic irradiation is characterized in that it comprises the step of irradiating a solution containing a surface active protein and a substance capable of generating active oxygen species upon ultrasonic radiation with ultrasonic waves to thereby form foams or bubbles and the step of selecting those bubbles which have a size within the desired range from among the bubbles formed.

In the selection step, the bubbles having a diameter within the desired range are selected using a filter or a centrifuge. The thus-selected bubbles each is enclosed by a protein membrane (shell) with a gas included in the membrane inside, and the shell-constituting protein membrane contains the substance capable of generating active oxygen species upon ultrasonic irradiation.

The tumor treatment method according to the invention comprises the step of administering a medicinal preparation in the form of shells each having an outside diameter not smaller than 0.1 μm but not greater than 5 μm and enclosing a gas in the inside and containing a substance capable of generating active oxygen species upon ultrasonic irradiation to a patient, and the step of irradiating the affected part of the patient with an ultrasound having a fundamental frequency and an ultrasound having the second-harmonic frequency superposed on each other. The fundamental waves preferably have a frequency within the range of 0.1 to 1.5 MHz. When stabilized bubbles not smaller than 0.1 μm but not greater than 1 μm are used as the medicinal preparation, they can be accumulated at the tumor site.

BRIEF DESCRIPTION OF THE DRAWINGS

FIG. 7 shows the tumor growth inhibiting effect of a medicinal preparation according to the invention when combined with ultrasonic irradiation;

FIG. 9 shows the tumor growth inhibiting effect of a medicinal preparation according to the invention when combined with ultrasonic irradiation;

DETAILED DESCRIPTION OF THE PREFERRED EMBODIMENTS

Several preferred modes of embodiment of the present invention are described in the following referring to the accompanying drawings. The applicability of the invention is not limited to the embodiments mentioned below.

EXAMPLE 1

The production of a medicinal preparation according to the invention in which a stabilized gas with a protein as a shell is used as a carrier and hematoporphyrin dimer is contained in the shell is described in the following by way of example.

Hematoporphyrin dimer (0.1 g) was added to 100 ml of an aqueous solution containing 5% (w/v) of human serum albumin, and the mixture was stirred. After removal, by dialysis, of the portion of hematoporphyrin dimer that had not been adsorbed on albumin, the mixture was irradiated with an ultrasound for 5 minutes using an ultrasonic disrupter (20 kHz) to cause formation of bubbles. On that occasion, the atmosphere was adjusted so that the gas inside the carrier might consist of air or a gas sparingly soluble in water. A perfluorocarbon $C_nF_{2n+2}$ (n=1 to 9) or $SF_6$ was used as the sparingly soluble gas or the liquid serving as a source of such gas. After ultrasonic irradiation, bubbles greater in size were removed by means of a 2-μm filter, and the desired stabilized bubbles submicron in diameter (maximum distribution particle diameter: 0.7 μm) were obtained.

Generally, when the frequency of the ultrasound is low (20 to several hundred kHz), the main action of cavitation is a mechanical one and, when, conversely, the frequency is high (around 1 MHz), the main action is a chemical one. In the latter case, the chemical action causes generation of active oxygen species and thereby oxidation and reduction occur. The reason why a low-frequency ultrasound was used for bubble formation in this example is that hematoporphyrin dimer might be prevented from being denatured, among others, by a chemical action. Conversely, in carrying out the therapy, this active oxygen species is important and, therefore, a low ultrasonic frequency of about 20 kHz is not adequate. Generally, bubbles about several micrometers or smaller in diameter as occurring in a liquid are high in surface area/volume ratio, so that, from the surface tension viewpoint, it is advantageous for a plurality of them to combine together to form a larger bubble as compared with the occurrence as a plurality of bubbles. By reducing this surface tension, it becomes possible for minute bubbles to stably occur. Albumin used in this example can function as a surface active agent and can lower the surface tension. Owing to this activity, the bubbles having a structure such that albumin constitutes shells are stabilized.

Figure 1:
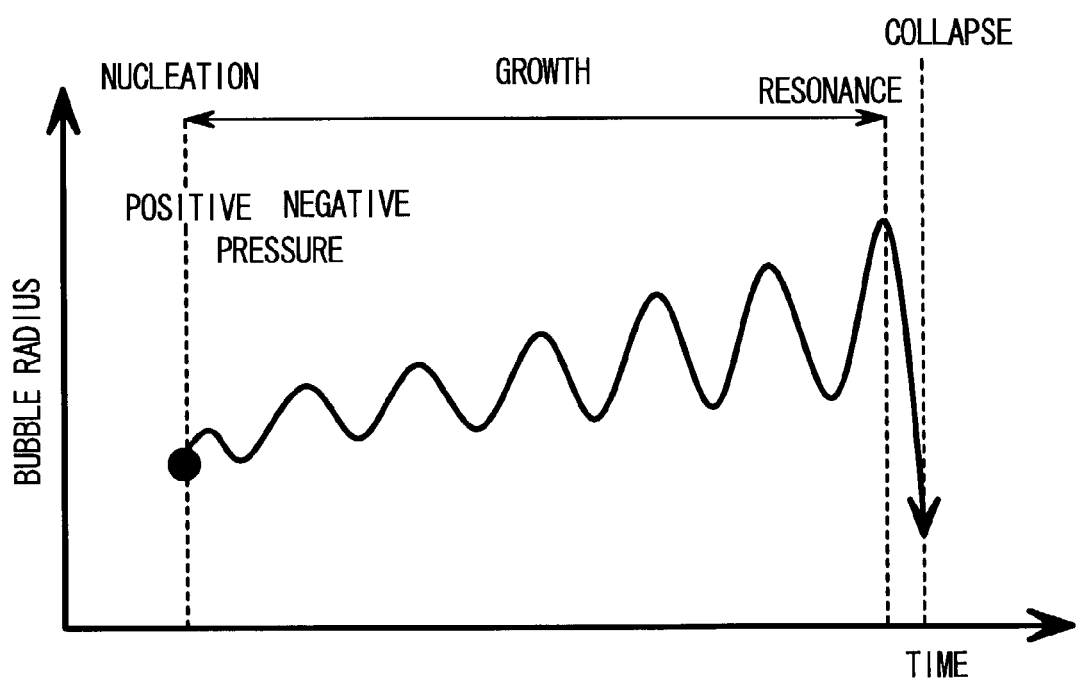
FIG. 1 is a graph showing the process of acoustic cavitation.
Figure 2:
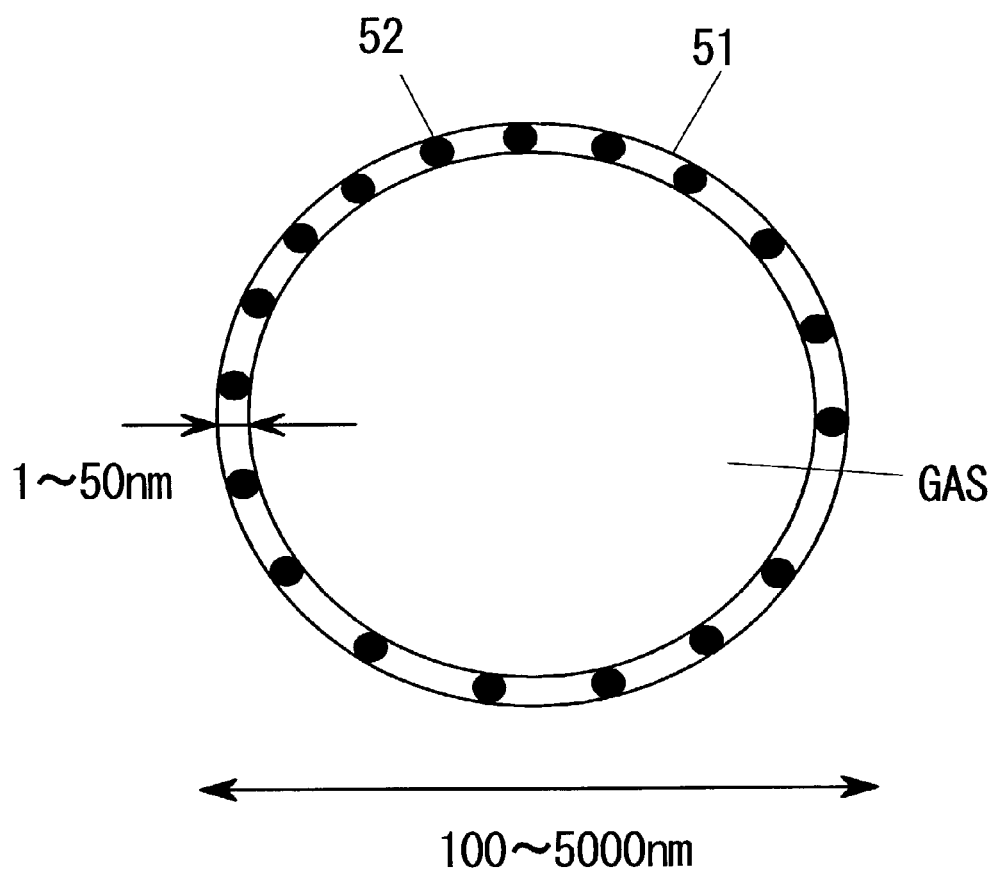
FIG. 2 is a diagram showing the conceptual structure of a medicinal preparation according to the present invention.

FIG. 2 is a schematic representation of the conceptual structure of a medicinal preparation according to the invention. A shell 51 and a bubble stabilized by the shell constitute a carrier, and the structure of the medicinal preparation is such that the shell 51 of this carrier contains a substance 52 (in this example, hematoporphyrin dimer) capable of generating active oxygen species upon ultrasonic irradiation. The wall thickness of the shell 51 may vary depending on the constituent substance but is about 1 to 50 nm and this is very thin as compared with bubbles submicron or of micron order in diameter.

Figure 3:
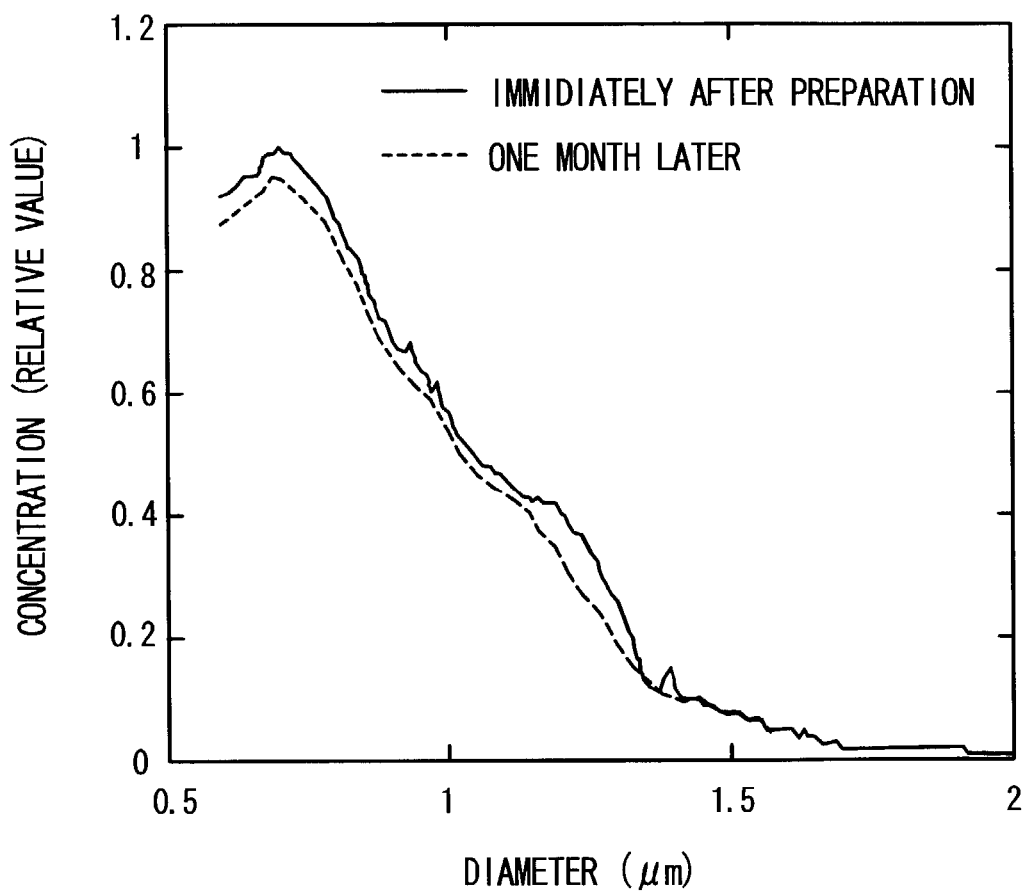
FIG. 3 is a graph showing the particle size distribution of a medicinal preparation according to the invention.

For determining and confirming the size and number of bubbles, a Coulter counter was used which measures the size and number distribution of bubbles in a solution as the change in electric resistance value as caused upon passage of bubbles through a minute hole being used as an index. The medicinal preparation obtained in the form of a solution was stored at 4° C. and, after one month, the particle diameter distribution was examined using a Coulter counter and it was confirmed that almost no change had occurred. The particle size distribution immediately after preparation and that after one month are shown in FIG. 3. When human serum globulin, human hemoglobin, saponin and protein Z were used each as the protein in lieu of human serum albumin, similar results were obtained.

The results of tests performed for evaluating the characteristics of the medicinal preparation thus obtained are now described.

Test Example 1

Figure 4:
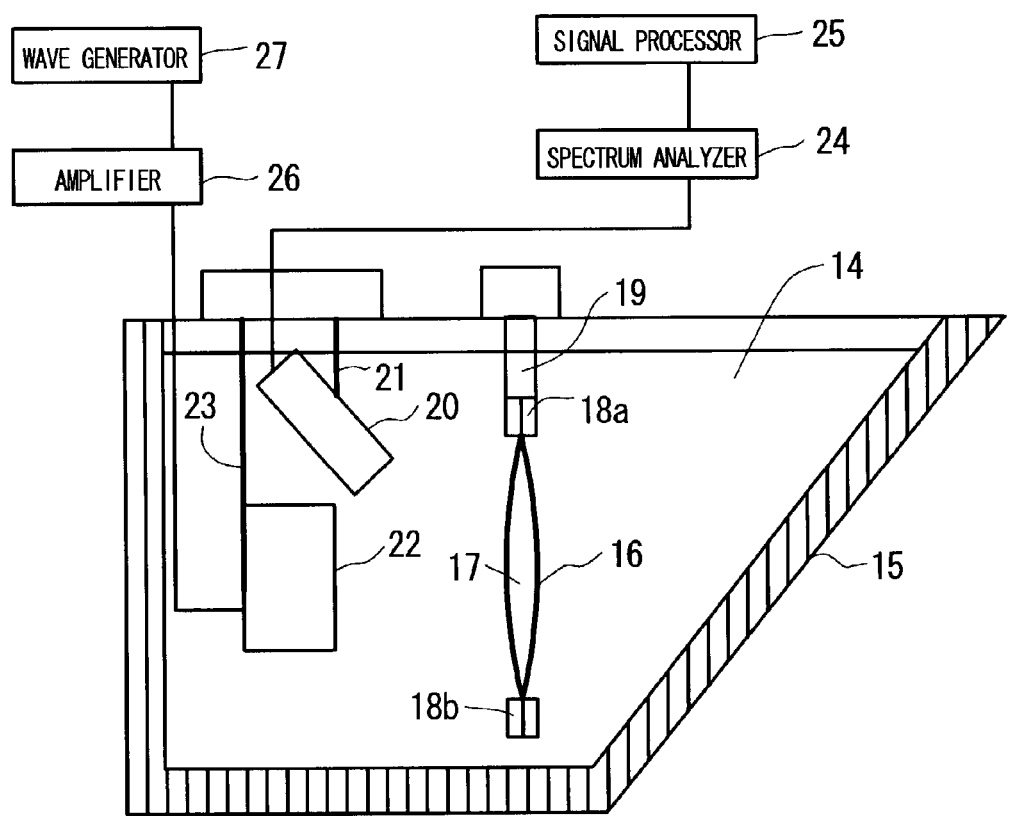
FIG. 4 is a diagram showing an experimental system for measuring the effect of a medicinal preparation according to the invention in lowering the threshold of acoustic cavitation.

Using the experimental apparatus schematically shown in FIG. 4, the effect of the medicinal preparation of the invention in lowering the threshold of cavitation in combined use with an ultrasound was measured. As an index of cavitation, the intensity of the frequency component (subharmonic) half in frequency of the ultrasound irradiated, which component is characteristic of cavitation and is directly involved in the vibration of bubbles was employed.

Phosphate-buffered saline (pH=7.4) containing the medicinal preparation of the invention to be used in combination with an ultrasound in a concentration of 50 mg/ml was used as a sample solution 17. A polyethylene bag 16 (30 mm×25 mm) containing the sample solution 17 as packed therein was fixedly mounted on a fixing device 19 by means of pinch cocks 18a and 18b and placed in a water tank 15 filled with degassed water 14. A sinusoidal wave with a frequency of 1 MHz and a sinusoidal wave with a frequency of 2 MHz were synthesized in a waveform generator 27, amplified in an amplifier 26 and inputted into a planar ultrasonic transducer 22 held by a fixing device 23. Ultrasonic waves resulting from superposition of the frequencies 1 MHz and 2 MHz were simultaneously irradiated from the ultrasonic transducer 22 for 1 to 2 minutes and, during ultrasonic irradiation, the acoustic signals from the sample solution 17 were measured by means of a hydrophone 20 held by a holder 21. The acoustic signals detected by the hydrophone 20 were inputted into a spectrum analyzer 24, and the signal component of 500 kHz (a subharmonic of 1 MHz) was extracted at one-second intervals and the time-average root mean square value of the subharmonic component was determined by means of a signal processor 25. The time-average root mean square value of the subharmonic component was defined as the subharmonic intensity and used as an index of the magnitude of acoustic cavitation. In a control experiment, phosphate-buffered saline (pH=7.4) was used in lieu of the phosphate-buffered saline (pH=7.4) containing the therapeutic preparation of the present invention used in combination with the ultrasound.

Figure 5:
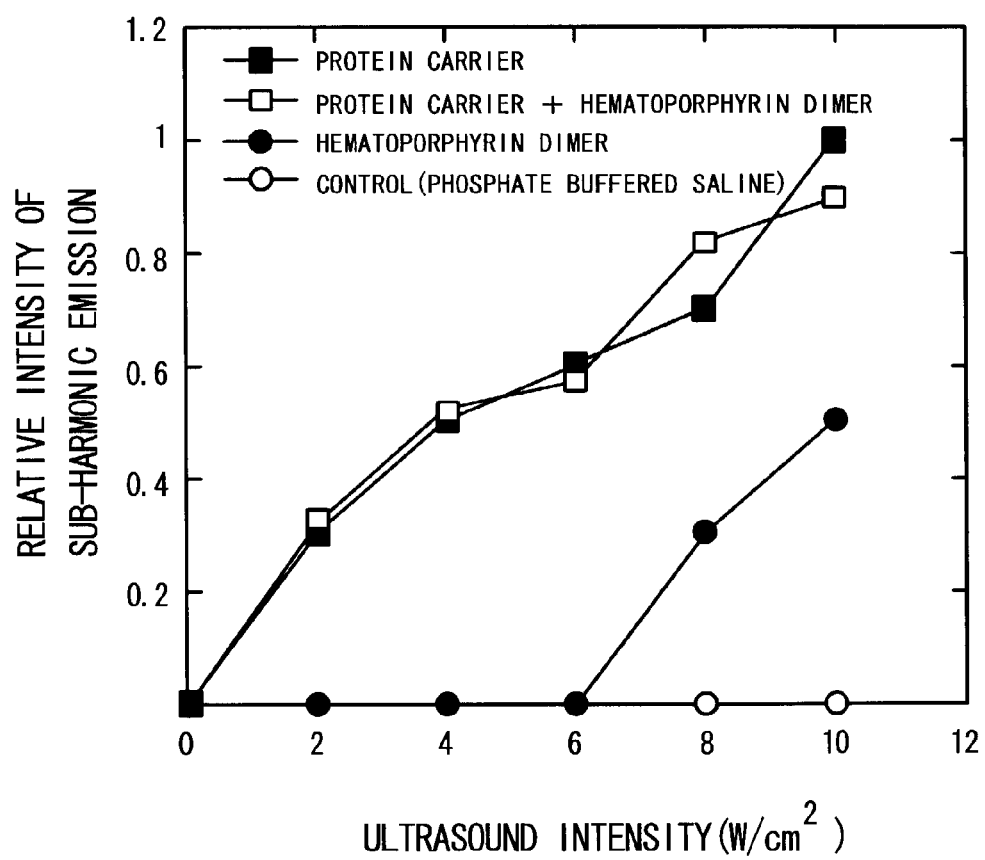
FIG. 5 is a graph showing the effect of a medicinal preparation according to the invention in lowering the threshold of acoustic cavitation.

Examples of the test results are shown in FIG. 5. The therapeutic agent used in combination with the ultrasound was composed of the protein carrier consisting of albumin plus hematoporphyrin dimer as shown in Example 1. The results obtained with the protein carrier alone are also shown.

With the therapeutic agent plus protein carrier used in combination with the ultrasound, acoustic cavitation occurred at about 2 W/cm$^2$ and above and, with the increase in sound intensity, the subharmonic intensity increased. On the contrary, in the control experiment, no acoustic cavitation occurred even at 10 W/cm$^2$. With hematoporphyrin dimer alone, acoustic cavitation occurred at 8 W/cm$^2$ and above. From these facts, it is seen that the therapeutic agent of the present invention can lower the threshold of acoustic cavitation to a level one fifth or lower as compared with the control or to a level about one fourth as compared with the single use of hematoporphyrin dimer. Since this threshold lowering effect is produced by the carrier protein, it is obvious that the same effect can be obtained when other medicinally active substances than hematoporphyrin dimer, for example photosensitizers in xanthene dye groups. When human serum globulin, human hemoglobin, saponin or protein Z was used as the protein carrier in lieu of human serum albumin, similar results were obtained.

Test Example 2

Figure 6:
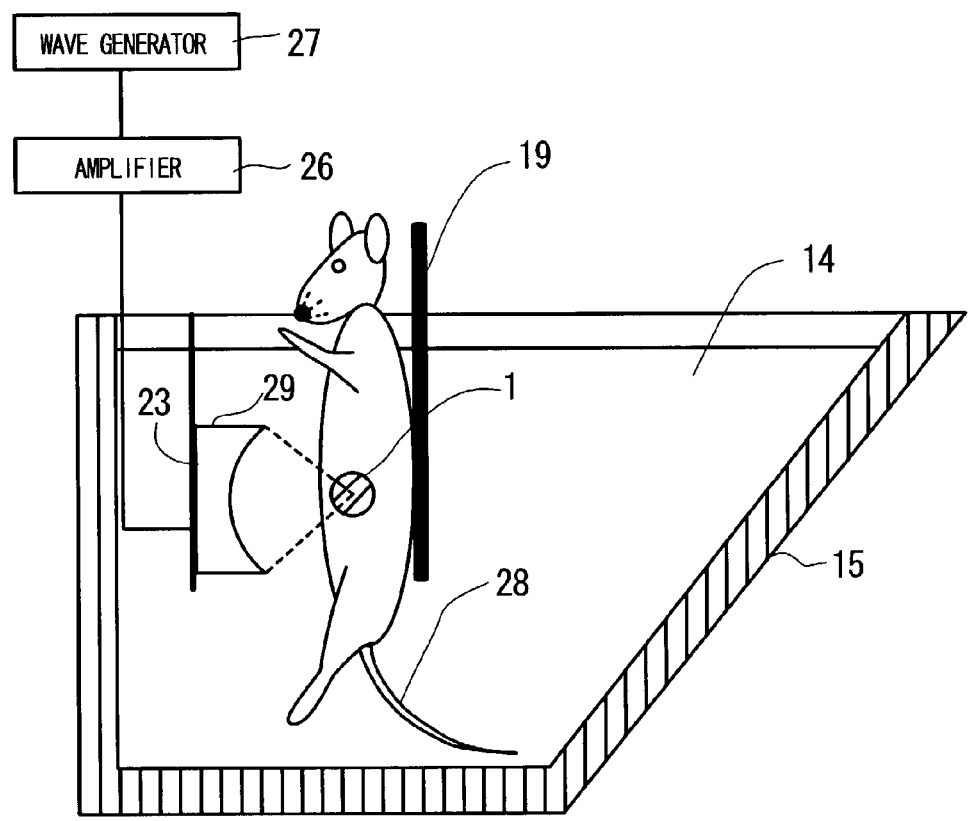
FIG. 6 is a diagram showing an experimental system for measuring the tumor growth inhibiting effect of a medicinal preparation according to the invention when combined with ultrasonic irradiation.

An experiment in mouse tumor treatment was carried out using ultrasonic irradiation by the second harmonic superposing technique. The tumor growth inhibition test was carried using an experiment system shown in FIG. 6, as follows. Colon 26 cells were transplanted subcutaneously into the abdomen of seven-week-old male BALB/c mice (groups of 3 animals) and then, at the stage at which he tumor had grown to a diameter of about 1 cm, the therapeutic agent to be used in combination with an ultrasound according to the invention was intravenously administered at a dose of 50 mg/kg of body weight. Each mouse 28 fixed and anesthesized on a fixing device 19 was immersed in a water tank 15 filled with degassed water 14, and the fixing device was moved so that the tumor of about 1 cm in diameter as transplanted subcutaneously might come to the position of the focus of a focused ultrasonic transducer 29. Twelve hours after intravenous administration of the therapeutic agent according to the invention to be used in combination with an ultrasound, the tumor site was irradiated with an ultrasound of 0.5 MHz and an ultrasound of 1 MHz superimposedly for 5 minutes respectively at an intensity of 10 W/cm$^2$. On the day 14 after ultrasonic irradiation, the tumor 28 was weighed and the tumor growth inhibition percentage was calculated as follows:

$$\text{Tumor growth inhibition}(\%) = \frac{\text{average tumor weight in the control group} - \text{average tumor weight in the test group}}{\text{average tumor weight in the control group}} \times 100$$

In the control group, no ultrasound was irradiated after administration of the therapeutic agent according to the invention to be used in combination with an ultrasound after transplanting Colon 26 carcinoma cells into the mouse, or no ultrasonic irradiation was performed without administration of the therapeutic agent of the invention to be used in combination with an ultrasound after transplanting Colon 26 carcinoma cells into the mouse.

Examples of the results obtained by using the therapeutic agent of the invention are shown in FIG. 7. The rate of tumor growth inhibition (inhibition rate) as obtained by carrying out ultrasonic irradiation was 10.2% in the control experiment, while the inhibition rate obtained by using the combination of albumin and hematoporphyrin dimer as the therapeutic agent was 70.5%, namely the antitumor effect was as high as about 7 times.

EXAMPLE 2

An example of the production of a medicinal preparation in which hemoglobin was used as the carrier and Rose Bengal as a medicament carried in the carrier shell is now described.

Figure 8:
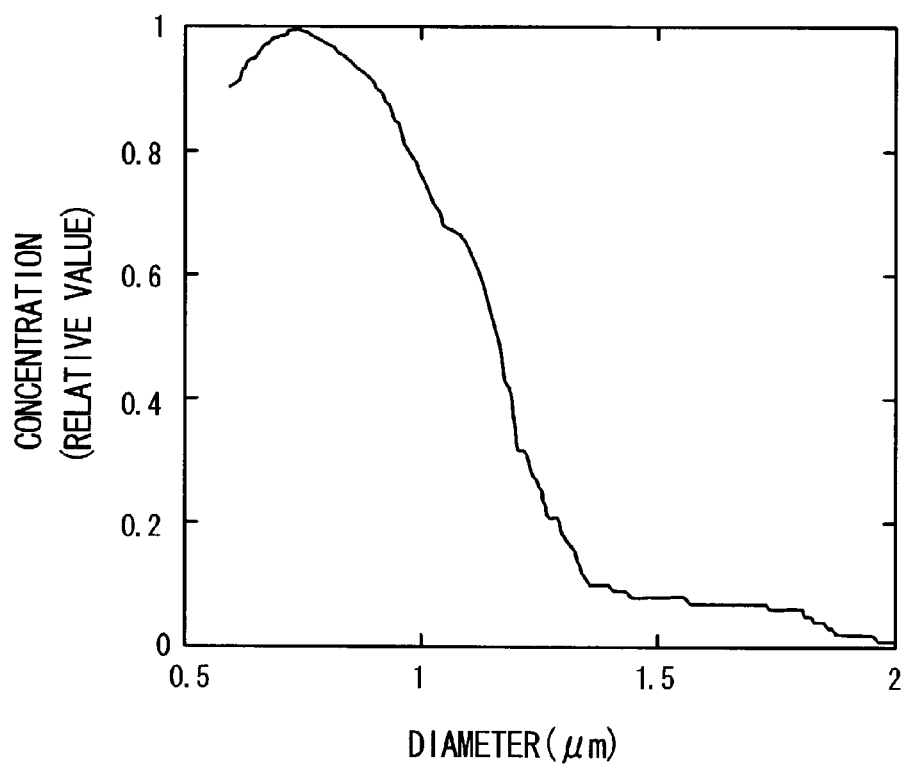
FIG. 8 is a graph showing the particle size distribution of a medicinal preparation according to the invention.

Rose Bengal (0.1 g) was added to 100 ml of an aqueous solution of 5% (w/v) of hemoglobin, and the mixture was stirred. After removal, by dialysis, of that portion of Rose Bengal that had not been adsorbed on albumin, bubbles were caused to form by 3 minutes of ultrasonic irradiation by means of an ultrasonic disrupter (20 kHz). After ultrasonic irradiation, stirring was continued for 30 minutes. Remnants larger in size were removed by using a 2-µm filter, whereby a medicinal preparation having the desired submicron size was obtained. The bubble size and concentration were confirmed using a Coulter counter. An example of the results is shown in FIG. 8.

The therapeutic agent prepared in this example was examined for its therapeutic effect on murine tumor using the same experimental system as used in Test Example 2 in Example 1. When ultrasonic irradiation was carried out, the tumor growth inhibition rate was 10.2% in the control experiment while the inhibition rate was 60.2% when the combination of hemoglobin and Rose Bengal was used. The latter rate is about 6 times the former rate. When human serum albumin, human serum globulin, saponin or protein Z was used as the protein in lieu of human hemoglobin, similar results were obtained.

EXAMPLE 3

An example of the production of a medicinal preparation comprising a protein as the carrier and Rose Bengal in admixture with the carrier is now described.

Bubbles were caused to form by 5 minutes of ultrasonic irradiation of 100 ml of an aqueous solution containing 5% (w/v) of human serum albumin by an ultrasonic disrupter (20 kHz). On that occasion, the atmosphere was adjusted so that the gas inside the carrier might consist of air or a gas sparingly soluble in water. A perfluorocarbon $C_nF_{2n+2}$ (n=1 to 9) or $SF_6$ was used as the sparingly soluble gas or the liquid serving as a source of such gas. After ultrasonic irradiation, bubbles greater in size were removed by means of a 2-µm filter, and the desired stabilized bubbles were obtained. Thereafter, 10 ml of this carrier dispersion was supplemented with 5 ml of a solution of 0.1 g of Rose Bengal in 100 ml of phosphate-buffered saline, and the mixture was gently stirred to give the desired medicinal preparation comprising the protein carrier and Rose Bengal admixed with the carrier.

EXAMPLE 4

An example of the tumor treatment using a therapeutic agent comprising stabilized bubbles with a protein constituting a shell of each bubble and serving as a carrier and hematoporphyrin dimer contained in the shell and to be used in combination with an ultrasound, and ultrasonic irradiation by the second harmonic superimposition technique is now described.

Figure 10:
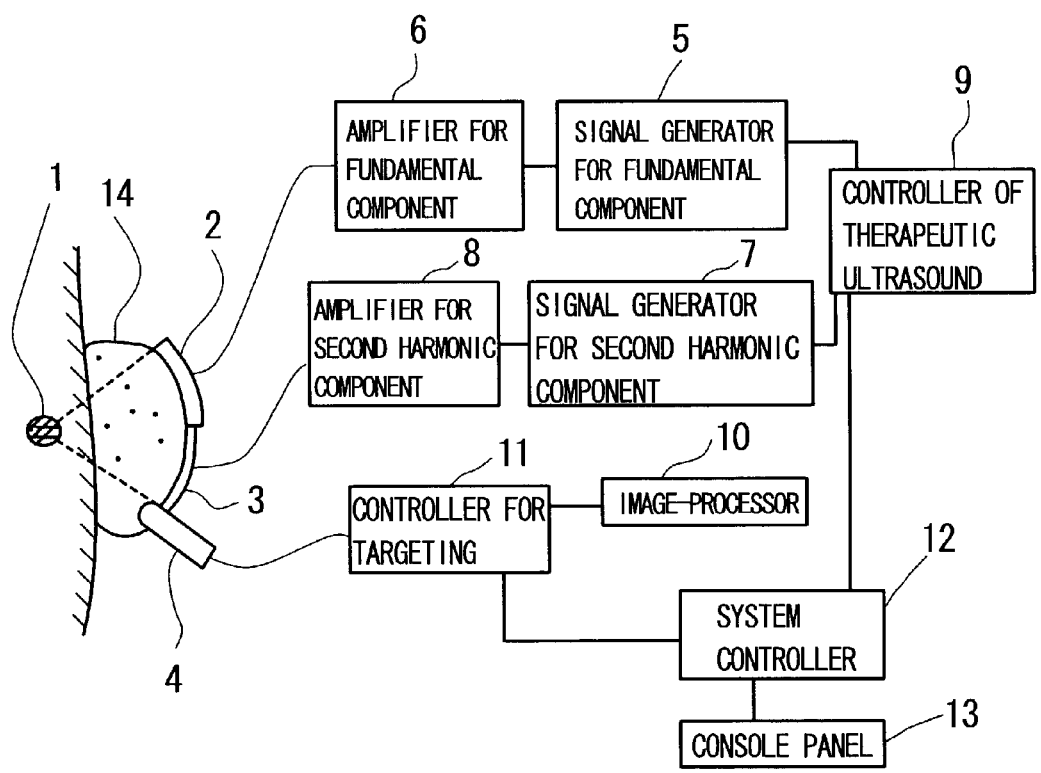
FIG. 10 is a diagram showing the constitution of a therapeutic apparatus to be used in combination with a medicinal preparation according to the invention.

An example of the constitution of a therapeutic apparatus for carrying out the treatment with the therapeutic agent according to the invention in combination with an ultrasound is shown in FIG. 10. This treatment apparatus is constituted such that ultrasonic irradiation can be carried out by the second harmonic superposion technique so that an ultrasound with a fundamental frequency (fundamental waves) may superpose on an ultrasound with a double frequency (second harmonic waves) at the focus thereof. This second harmonic superposition technique is suited for use in causing cavitation. The apparatus is constituted such that sinusoidal signals are generated by signal generators 5 and 7 under the control of a therapeutic ultrasound controller 9 and amplified by amplifiers 6 and 8 and ultrasonic irradiation is carried out by applying an alternating voltage to a transducer 2 for fundamental waves and a transducer 3 for second harmonic waves. The ultrasonic irradiation is carried out via degassed water 14. The ultrasonic echo image obtained by a probe 4 for ultrasonic diagnosis under the control of a controller 11 for targeting is displayed, together with the relevant therapeutic guidance, on an image processor 10. Information concerning the high application voltage, the site of the focus and so forth is given to the therapeutic ultrasound controller 9 when the system controller 12 is controlled by means of the console panel 13.

As for the procedure of treatment, position adjustment is made according to imaging diagnosis using an ultrasonic diagnostic probe 4 for targeting so that the transducer 2 for fundamental waves and the transducer 3 for second harmonic waves may focus on the tumor 1. While controlling the therapeutic ultrasound controller 9 by the system controller 12 and thus confirming the site for therapy, a therapeutic ultrasound is irradiated. Since the cavitation threshold is high when the frequency is high and a frequency of not higher than 3 MHz is suited for practical use, a frequency of 0.1 to 1.5 MHz is desirably used for the fundamental wave and a frequency of 0.2 to 3 MHz for the second harmonic. The ultrasound intensity is changed within the range of 5 to 100 $W/cm^2$ according to the site to be irradiated.

In this treatment, the therapeutic effect is mainly produced by cavitation upon ultrasonic irradiation and by oxidative destruction of such constituents of tumor cells as the cell membrane by active oxygen species generated by hematoporphyrin dimer upon cavitation. In addition, the contribution of the thermal effect resulting from absorption of the ultrasonic energy by the tissues can also be expected. In this therapy, the technique of superposing the fundamental wave and the second harmonic thereof on each other at the site of treatment for the purpose of causing cavitation at a lower energy level.

Figure 11:
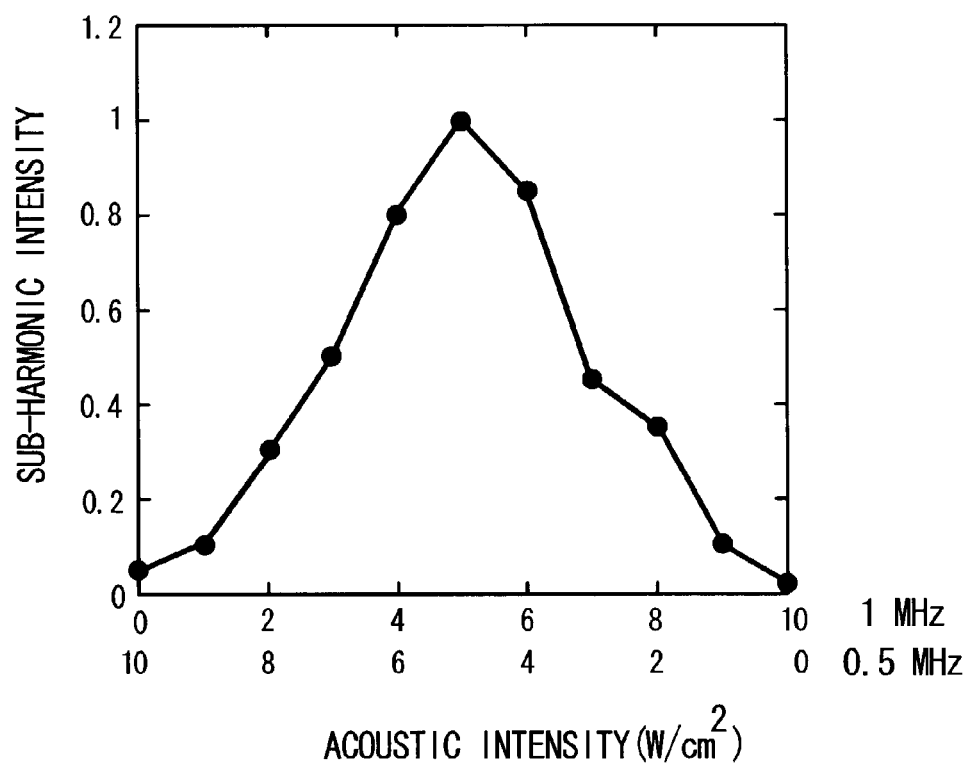
FIG. 11 is a graph showing the cavitation generated upon irradiation with an ultrasound at fundamental frequency and an ultrasound at second-harmonic frequency superposed on each other.

FIG. 11 shows an example of the effect of the technique of superposing the fundamental wave and the second harmonic thereof on each other in the experimental system shown in Test Example 1. As shown in FIG. 11, the fundamental wave (0.5 MHz) alone or the second harmonic (1.0 MHz) alone did not cause subharmonic generation, hence did not cause cavitation, while the superposition of them resulted in cavitation and, in particular when the superposition was carried out at a ratio of 1:1, the most intensive cavitation was observed.

As explained hereinabove, the medicinal preparation of the invention, when combined with an ultrasound, produced high levels of cavitation causing and cavitation-caused active oxygen species generating effects in vivo, and thus enables the intravascular or tumor treatment and/or diagnosis with high efficiency.

What is claimed is:

1. A medicinal preparation comprising
a shell which has an internal space enclosed by the shell;
a gas which is enclosed in the internal space; and
a substance which is disposed in the shell phase, wherein the substance generates active oxygen species via acoustic cavitation caused from the gas in the internal space being exposed to ultrasonic irradiation;
wherein the shell has a spherical form with an outside diameter of not smaller than 0.1 μm but not greater than 5 μm; and
wherein the substance that generates active oxygen species upon ultrasonic irradiation is selected from among photosensitizing antitumor agents, xanthene dyes and porphyrin dyes.

2. A tumor treatment method comprising the step of:

administering, to a patient, a medicinal preparation comprising a shell having an outside diameter not smaller than 0.1 μm but not greater than 5 μm and having an internal space enclosed by the shell, and a gas being enclosed in the internal space, and a substance being disposed in the shell phase, and the substance generates active oxygen species via acoustic cavitation caused from the gas in the internal space being exposed to ultrasonic irradiation; and irradiating an affected site of the patient with an ultrasound at a fundamental frequency and an ultrasound at the second-harmonic frequency relative to the fundamental ultrasound in the manner of superposition on each other.

3. A tumor treatment method as claimed in claim 2, wherein the fundamental wave has a frequency of 0.1 to 1.5 MHz.

* * * * *